(12) United States Patent
Shingai et al.

(10) Patent No.: US 6,384,267 B1
(45) Date of Patent: May 7, 2002

(54) PROCESS FOR PRODUCING HYDROXYALKYL (METH) ACRYLATES

(75) Inventors: Yasuhiro Shingai; Masatoshi Ueoka, both of Himeji; Junya Watanabe; Hirohisa Kubota, both of Yokohama, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/503,087

(22) Filed: Feb. 14, 2000

(30) Foreign Application Priority Data

Feb. 17, 1999 (JP) .............................. 11-039097

(51) Int. Cl.$^7$ .............................................. C07C 67/26
(52) U.S. Cl. ..................................................... 560/209
(58) Field of Search ......................................... 560/209

(56) References Cited

U.S. PATENT DOCUMENTS

| | | | | |
|---|---|---|---|---|
| 2,929,835 A | * | 3/1960 | Hayes et al. ................. | 560/209 |
| 3,215,731 A | * | 11/1965 | Bearden et al. ............. | 560/224 |
| 3,340,295 A | | 9/1967 | Wheeler et al. | |
| 3,373,188 A | * | 3/1968 | Svoboda ....................... | 560/4 |
| 3,804,884 A | | 4/1974 | Jeffrey et al. | |
| 3,875,211 A | * | 4/1975 | Steckler ....................... | 560/209 |
| 4,365,081 A | * | 12/1982 | Shimizu et al. ............. | 560/209 |
| 4,970,333 A | | 11/1990 | Rabon, Jr. et al. | |
| 5,354,896 A | | 10/1994 | Pike et al. | |

FOREIGN PATENT DOCUMENTS

| | | |
|---|---|---|
| EP | 0 444 643 | 9/1991 |
| EP | 0 460 253 | 12/1991 |
| GB | 1003346 | 9/1965 |
| JP | 41-13019 | 7/1941 |
| JP | 4-49265 | 2/1992 |
| JP | 4-349941 | 12/1992 |

* cited by examiner

Primary Examiner—James O. Wilson
Assistant Examiner—Taylor V Oh
(74) Attorney, Agent, or Firm—Oblon, Spivak, McClelland, Maier & Neustadt, PC

(57) ABSTRACT

In a process for producing hydroxyalkyl (meth)acrylates by the reaction of (meth)acrylic acid with an alkylene oxide, a thermally and chemically stable anion exchange resin is used as a catalyst, which resin contains a repeating unit represented by the following formula (1) as a component:

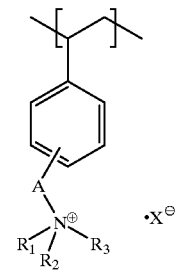

(1)

wherein A is a straight chain alkylene group having 3 to 8 carbon atoms, each of $R^1$, $R^2$, and $R^3$ is a hydrocarbon group or an alkanol group having 1 to 4 carbon atoms, which may be substituted with a hydroxyl group, $X^-$ is a counter ion coordinated with an ammonium group, where the substituent A with the ammonium group may be substituted at any position of a benzene ring, and the benzene ring may be substituted with an alkyl group or a halogen atom. The process can economically efficiently produce hydroxyalkyl (meth)acrylates without disadvantages such as deterioration in properties of a distillation residue.

8 Claims, No Drawings

PROCESS FOR PRODUCING HYDROXYALKYL (METH) ACRYLATES

This application is based on patent application No. 11-39097 filed in Japan, the contents of which is hereby incorporated by reference.

BACKGROUND OF THE INVENTION

1. Field of the Invention

The present invention relates to a process for producing hydroxyalkyl (meth)acrylates. Specifically, the present invention relates to an improved process which can commercially advantageously yield hydroxyalkyl (meth) acrylates from (meth)acrylic acid and alkylene oxides.

2. Description of the Prior Art

Hydroxyalkyl (meth)acrylates have been obtained by reacting (meth)acrylic acid with an alkylene oxide in the presence of a homogenous catalyst. Such homogenous catalysts include ferric chloride, iron hydroxide, and other iron compounds; chromium chloride and amine compounds; trialkyl amine, pyridine. However, such catalysts cannot be significantly separated from reaction mixtures for recycling, and are disadvantageous in cost efficiency.

These catalysts also serve to accelerate polymerization of the produced hydroxyalkyl (meth) acrylates. When the catalyst is transported into a distillation system for purification, it invites a distillation residue to polymerize thereby to become a gel, which will cause a blockage of equipment or other troubles.

As a possible solution to these problems, processes of using anion exchange resins as heterogenous catalysts have been proposed. For example, Japanese Examined Patent Publication No. 41-13019 discloses a process of using a catalyst comprising an ion exchange resin, most of whose ionic active groups are quaternary ammonium groups. Typical examples of the ion exchange resins used in this process are "DIAION® SA10A" (trade name: a styrene type anion exchange resin manufactured by Mitsubishi Chemical Corporation, Japan), and "Amberlite IRA-400" (trade name: a styrene type anion exchange resin manufactured by Rohm & Haas Co.).

Japanese Unexamined Patent Publication No.4-49265 discloses a process of using a catalyst comprising a strongly basic macroporous anion exchange resin having an acrylic backbone. Typical ion exchange resins used in the process include "Amberlite IRA-958 (trade name: an anion exchange resin manufactured by Rohm & Haas Co.), and "Lewatit AP-247-A" (trade name: an anion exchange resin manufactured by Bayer AG).

However, such known styrene type or acrylic type anion exchange resins have the following disadvantages.

The anion exchange resins having a trimethylammonium groups are known to be insufficient in heat resistance, and are believed to be used at temperatures of at highest about 50° C. to 70° C. In contrast, in the commercial production of hydroxyalkyl (meth)acrylates by the reaction of (meth) acrylic acid with an alkylene oxide, an optimum reaction temperature is 50° C. or higher, and reaction temperatures as higher as possible are desirable to increase reaction rates to thereby improve reaction yields. The anion exchange resins which are insufficient in thermal stability cannot be effectively used as catalysts.

Specifically, the anion exchange resins under reaction conditions at high temperatures are liable to release the trimethylammonium group serving as a reactive group, which rapidly deteriorates the catalytic activity with the passage of reaction time. In addition, reaction products are contaminated by trimethylamine derived from the anion exchange resins, which causes, for example, deteriorated coloring tone of end products.

In order to improve the heat resistance of the anion exchange resins, an anion exchanger has been proposed in Japanese Unexamined Patent Publication No. 4-349941, which anion exchanger comprises a benzene ring bonded through a polymethylene chain with an ammonium group.

When the polyalkylene chain is an ethylene chain the resin is liable to be subjected to Hofmann degradation (an elimination reaction of trimethylamine). If a dimethyl group is introduced at the α-position to yield 1,1-dimethylethylene chain to thereby inhibit the Hofmann degradation, the heat stability of the anion exchange group is deteriorated due to the steric hindrance between the both methyl groups at the α-position [J. Appl. Polym. Sci., 8.1659(1964)].

The processes of using known ion exchange resins as catalysts, in which the chemical or thermal stability of the ion exchange resins is inferior, cannot commercially yield hydroxyalkyl (meth)acrylates from (meth)acrylic acid and alkylene oxides in good yields.

SUMMARY OF THE INVENTION

Accordingly, an object of the present invention is to solve the problems inherent to the conventional equivalents and to provide a process for economically efficiently producing hydroxyalkyl (meth)acrylates without disadvantages such as deterioration in properties of a distillation residue (gelation), by the use of a specific anion exchange resin having satisfactory thermal and chemical stability as a catalyst.

Specifically, in the invented process for producing hydroxyalkyl (meth)acrylates by the reaction of (meth) acrylic acid with an alkylene oxide, an anion exchange resin is used as a catalyst, which anion exchange resin containing a repeating unit represented by the following formula (1) as a component:

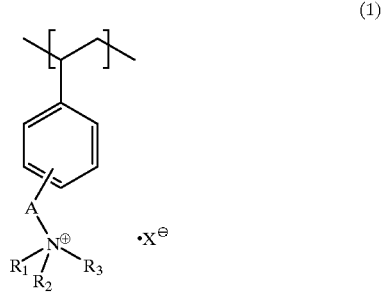

(1)

wherein A is a straight chain alkylene group having 3 to 8 carbon atoms, each of $R^1$, $R^2$, and $R^3$ is a hydrocarbon group or an alkanol group having 1 to 4 carbon atoms, which may be substituted with a hydroxyl group, $X^-$ is a counter ion coordinated with an ammonium group, where the substituent A with the ammonium group may be substituted at any position of a benzene ring, and part of hydrogen atoms bonded to the benzene ring may be substituted with an alkyl group or a halogen atom.

DESCRIPTION OF THE PREFERRED EMBODIMENT

The present invention has a feature in that an anion exchange resin is used as a catalyst, which resin contains a repeating unit of the formula (1) as a component. As is apparent from the formula (1), the anion exchange resin for use in the invention can solve the problem of insufficient heat resistance in conventional anion exchange resins, by the introduction of a straight alkylene chain between an ion exchange group and a benzene ring. The anion exchange resin can therefore make (meth)acrylic acid to efficiently react with an alkylene oxide and can efficiently produce a hydroxyalkyl (meth)acrylate even at relatively high reaction temperatures.

The anion exchange resin for use in the invention having a repeating unit of the formula (1) is a polymer that is insoluble in a reaction system (a system in which reaction materials and products are present) of (meth) acrylic acid and an alkylene oxide. The substituent A in the formula (1) is a straight chain alkylene group having 3 to 8 carbon atoms.

The straight chain alkylene group A bonded to the ion exchange group is an essential element to improve the heat resistance of the ion exchange resin. If the number of carbons in the straight chain alkylene group A exceeds the above defined range, the constitutive unit of the formula (1) is to have an excessively large molecular weight, and an ion exchange capacity per unit mass is decreased to reduce the catalytic activity. Accordingly, the straight chain alkylene group A should have eight or less carbon atoms, preferably six or less carbon atoms. However, if the alkylene group A is an ethylene group or methylene group having two or less carbon atoms, the heat resistance is insufficient and a sustained satisfactory catalytic activity cannot be obtained. The straight chain alkylene group A must have three or more carbon atoms. Typically preferable examples of the alkylene group A are propylene group, butylene group, and pentylene group.

The alkylene group A having the ion exchange group may be substituted at any position of the benzene ring. The benzene ring in the formula (1) may be substituted with an alkyl group and/or a halogen atom. Such alkyl group include, but are not limited to, methyl group and ethyl group, and the halogen atom includes, for example, chlorine, bromine, and iodine atoms.

Each of groups $R^1$, $R^2$, and $R^3$ in the group $[NR^1R^2R^3]$ serving as an anion exchange group is an alkyl group, or a hydroxyethyl group or another alkanol group having 1 to 4 carbon atoms, and may have a hydroxyl group as a substituent. These groups may be either different from one another, or identical to one another partially or totally. Specifically preferred group $[NR^1R^2R^3]$ is trimethylammonium group in which all of $R^1$, $R^2$, and $R^3$ are methyl groups each having one carbon atom.

The ion $X^-$ in the formula (1) coordinates, as a counter ion, to the ammonium group serving as an ion exchange group. The counter ion includes, but is not limited to, $Cl^-$ and other halogen form ions, $OH^-$ form ion, and an alcoholate $(RO^-)$ form ion. Preferred form of the counter ion is a salt form of the reaction material (meth)acrylic acid for use in the invention and/or the reaction product hydroxyalkyl (meth)acrylate.

The anion exchange resins each containing a repeating unit of the formula (1) as a component can be obtained synthetically by a variety of processes. Such production processes include, but are not limited to, a process described in Japanese Unexamined Patent Publication No. 4-349941.

Specifically, the anion exchange resin can be obtained by the copolymerization of a copolymerizable component having a constitutive unit of the formula (1) with a crosslinkable monomer having an unsaturated hydrocarbon, and when necessary with a third monomer having an unsaturated hydrocarbon. The crosslinkable monomer having an unsaturated hydrocarbon has two or more ethylenically unsaturated double bonds that are radical-polymerizable and is an essential component to obtained the anion exchange resin as a crosslinked polymer insoluble in the reaction system (the system in which reaction materials and products are present). Such monomers include, but are not limited to, divinylbenzene, polyvinylbenzene, alkyldivinylbenzene, dialkyldivinylbenzene, ethylene glycol di(meth)acrylate, polyethylene glycol di(meth)acrylate, and polyethylene bis(meth)acrylamide. To ensure a sufficient physical strength in practice as a catalyst, the crosslinkable monomer(s) should preferably occupy 0.1% to 50% by mass, and more preferably 0.5% to 25% by mass in the overall monomers.

The unsaturated hydrocarbon-containing monomer for use as the third component includes, but is not limited to, styrene, an alkylstyrene, a polyalkylstyrene, a (meth)acrylic ester, (meth)acrylic acid, and acrylonitrile. The anion exchange resin can comprise the third component within the range not deteriorating the functions and properties required of the ion exchange resin. The content of the third component should be 50% by mass or less, and preferably 20% by mass or less in the overall polymerizable monomers.

The anion exchange resin for use as a catalyst in the invention can be molded into a wide variety of dimensions according to conventional technologies. The anion exchange resin should be preferably particle having a size of 100 μm to 10 mm to exhibit the catalytic activities effectively, but it can be used in the form of lump, powder, fiber, membrane (film), or others if necessary. For example, the anion exchange resin can be used in the form of an ion exchange membrane or an ion exchange fiber.

A reaction for producing a hydroxyalkyl (meth)acrylate from (meth)acrylic acid and an alkylene oxide with the use of the catalyst can be performed with a stirring batch-system reactor, a fixed bed reactor, a fluidized bed reactor, or another reactor. The reaction system may be either a batch system or a continuous system.

Alkylene oxides for use in the synthetic reaction is an alkylene oxides each having preferably 2 to 6, more preferably an alkylene oxides each having 2 to 4 carbon atoms and the most preferably ethylene oxide and propylene oxide.

The alkylene oxide is used in an amount of equivalent mole or more, and preferably one to five times by mole that of the (meth)acrylicacid. The reaction temperature usually ranges from 50° C. to 130° C., and preferably from 50° C. to 100° C. If the reaction temperature is lower than 50° C., the reaction rate is too low to obtain sufficient reaction efficiency. In contrast, if the reaction temperature exceeds 130° C., the reaction materials and/or products are liable to be polymerized.

The synthetic reaction is generally performed in a liquid phase under pressure. The reaction pressure should be preferably such a pressure as to maintain the reaction mixture as a liquid phase. The atmosphere in the reaction is not particularly limited, but should be preferably a nitrogen atmosphere or another inert atmosphere.

A polymerization inhibitor is usually used in the synthetic reaction in order to inhibit the polymerization of the produced (meth)acrylate. The polymerization inhibitor is not limited, and can be freely selected from polymerization inhibitors for use in reactions of this type.

Typical examples of such polymerization inhibitors include hydroquinone, methylhydroquinone, tert-butylhydroquinone, 2,6-di-tert-butylhydroquinone, 2,5-di-tert-butylhydroquinone, 2,4-dimethyl-6-tert-butylphenol, hydroquinone monomethyl ether, and other phenolic compounds; N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N,N'-diphenyl-p-phenylenediamine, N,N'-di-2-naphthyl-p-phenylenediamine, and other p-phenylenediamines; phenothiazine, thiodiphenylamine, and other amine compounds; copper dibutyl dithiocarbamate, copper diethyl dithiocarbamate, copper dimethyl dithiocarbamate, and other copper dialkyl dithiocarbamates; nitrosodiphenylamine, isoamyl nitrite, N-nitroso-cyclohexylhydroxylamine, N-nitroso-N-phenyl-N-hydroxylamine or its salt, and other nitroso compounds; 2,2,4,4-tetramethylazetidine-1-oxyl, 2,2-dimethyl-4,4'-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, 2,2,6,6-tetramethyl-4-benzoyloxypiperidine-1-oxyl, and other N-oxyl compounds.

The proportion of the polymerization inhibitor is usually about 0.001% to 1% by mass, and preferably about 0.01% to 0.5% by mass relative to the (meth)acrylic acid. The reaction can be performed in the presence of a solvent. Such solvents include, but are not limited to, benzene, toluene, xylene, hexane, heptane, petroleum ether and other solvents that are inert in the reaction.

According to the invention, hydroxyalkyl (meth)acrylates can be efficiently obtained in high yields by the coexistence of the anion exchange resin having a repeating unit of the formula (1) as a component in the reaction system.

The invention will be further illustrated in detail with reference to several inventive examples and comparative examples below which are not intended to limiting the scope of the invention.

EXAMPLES

In the following inventive examples and comparative examples, the term "meq/g" means an exchange capacity (milliequivalent) per dry resin weight. The exchange capacity of the anion exchange resin was determined according to "DIAION Manual" (issued by Mitsubishi Chemical Corporation, Japan). "DIAION® SA10A" (trade name, manufactured by Mitsubishi Chemical Corporation, Japan) was employed as an anion exchange resin for use in Comparative Example 1. The conversion rate and the residual rate after a heat test of the material (meth)acrylic acid were calculated according to the following equations.

Conversion rate (%)=[(mole number of consumed (meth)acrylic acid)/(mole number of supplied (meth)acrylic acid)]×100

Residual rate (%)=[(neutral salt-splitting capacity after heat test (meq/ml))×(volume of Cl-form resin after heat test)]/[(neutral salt-splitting capacity before heat test (meq/ml))×(volume of Cl-form resin before heat test)]×100.

PRODUCTION EXAMPLE 1

[Synthesis of ω-Halogenoalkylstyrene]

A total of 100 g of chloromethylstyrene was stirred with metallic magnesium in diethyl ether replaced with nitrogen at 0° C. for 3 hours to yield a magnesium complex. After replacing the solvent with nitrogen-replaced tetrahydrofuran, 1,3-dibromopropane and $Li_2CuCl_4$ were added dropwise to the magnesium complex at 0° C., and the reaction was continued at 0° C. for further 5 hours. The obtained products were then fractionated by distillation.

In the distillation process, 4-(4-bromobutyl)styrene (hereinafter simply referred to as "4-bromobutylstyrene") was obtained at 120° C. at a pressure of 0.3 Torr, and the yield on the basis of the material chloromethylstyrene was 35% by mass. The 4-bromobutylstyrene was identified according to an NMR technique described in "Journal of Polymer Science, Polymer Chemistry Edition; vol.20, 1982, pp.3015".

[Synthesis of Crosslinked ω-Halogenoalkylstyrene]

A total of 1.0 part by mass of azobisisobutyronitrile was added to 92.7 parts by mass of the above-obtained 4-bromobutylstyrene and 7.3 parts by mass of divinylbenzene for industrial use (purity: 55% by mass, the rest was mainly composed of ethylvinylbenzene), and the mixture was subjected to suspension-polymerization at 70° C. under a nitrogen atmosphere for 18 hours to yield crosslinked 4-bromobutylstyrene as polymer beads in yield of 90% by mass.

[Synthesis of Anion Exchange Resin]

The obtained crosslinked 4-bromobutylstyrene (100 parts by mass) was suspended in 300 parts by mass of dioxane, and was stirred for 2 hours for swelling. Trimethylamine in an amount of 3 molar equivalents to a bromo group was added dropwise to the suspension, and the resulting suspension mixture was subjected to a reaction at 50° C. for 10 hours to yield an anion exchanger. The anion exchanger was sufficiently washed with desalted water, and was then converted from a salt form to a Cl form to yield an anion exchange resin having the following properties.

neutral salt-splitting capacity: 1.10 meq/ml (3.65 meq/g)

Moisture content: 54.1% by mass

Degree of swelling: 3.32 ml/g

The above general properties were determined according to a method described in "Ion Exchange Resin" edited and written by Honda et al., Hirokawa Shoten, Japan, pp. 17–56.

COMPARATIVE SAMPLE 1

"DIAION® SA10A" (trade name: an anion exchange resin manufactured by Mitsubishi Chemical Corporation, Japan) used as Comparative Sample 1 had the following properties.

neutral salt-splitting capacity: 1.37 meq/ml

Moisture content: 45.4% by mass

The "DIAION® SA10A" is an anion exchange resin containing a repeating unit shown by the following formula as a component.

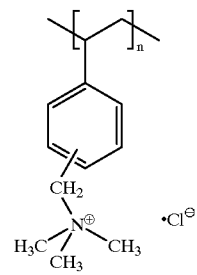

[Heat Test 1 of Anion Exchange Resin]

Fifty milliliters (50 ml) of the anion exchange resin obtained in Production Example 1 or the resin of Comparative Sample 1 was weighed. The weighed resin was regenerated by passing 500 ml of a 2 N sodium hydroxide aqueous solution, and the volume of the resulting resin was measured. The regenerated resin was subjected to a heat test in desalted water as described below.

Separately, a 60% by mass ethylene glycol (EG) aqueous solution or 100% by mass EG in an amount of 10 times that of the resin was passed through the regenerated resin, and the resin was then replaced with the EG solution. Each of the resins replaced with desalted water or the EG solution was placed in a glass tubular autoclave, and desalted water in an amount of 0.8 time by volume that of the OH⁻ form resin was added to the resin. The inside of the autoclave was then heated to 50° C. and nitrogen gas was passed therein for 30 minutes to eliminate dissolved oxygen in the autoclave.

The tubular autoclave was immersed in an oil bath, and was allowed to stand at temperatures shown in Tables 1 and 2 for 30 days or 90 days. After the heat test, the resin was regenerated with a 2 N sodium hydroxide aqueous solution, and the volume of the resulting resin was determined. Further, a 4% by mass sodium chloride aqueous solution in an amount of five times that of the resin was passed through the resin to convert the counter ion X⁻ to Cl form, and the volume and general properties of the resin were measured. The results are shown in Tables 1 and 2.

TABLE 1

| Anion Exchange Resin | EG Concentration (%) | Alkylene Group A | Residual Rate (%) |
|---|---|---|---|
| Production Example 1 | 60 | —(CH$_2$)$_4$— | 95 |
| Production Example 1 | 100 | —(CH$_2$)$_4$— | 89 |
| Comparative Sample 1 | 60 | —CH$_2$— | 62 |
| Comparative Sample 1 | 100 | —CH$_2$— | 43 |

TABLE 2

| Anion Exchange Resin | Alkylene Group A | Heat Test Condition | Residual Rate (%) |
|---|---|---|---|
| Production Example 1 | —(CH$_2$)$_4$— | 100° C., 30 days | 91 |
| Production Example 1 | —(CH$_2$)$_4$— | 100° C., 90 days | 82 |
| Production Example 1 | —(CH$_2$)$_4$— | 120° C., 30 days | 69 |
| Production Example 1 | —(CH$_2$)$_4$— | 120° C., 90 days | 68 |
| Comparative Sample 1 | —CH$_2$— | 100° C., 30 days | 63 |
| Comparative Sample 1 | —CH$_2$— | 100° C., 90 days | 52 |
| Comparative Sample 1 | —CH$_2$— | 120° C., 30 days | 16 |
| Comparative Sample 1 | —CH$_2$— | 120° C., 90 days | 3 |

PRODUCTION EXAMPLE 2

An anion exchange resin (an example in which A in the formula (1) had 7 carbon atoms) was obtained in the same manner as in Production Example 1, except that 1,6-dibromohexane was used instead of 1,3-dibromopropane in the synthesis of a ω-halogenoalkylstyrene. The resulting resin had the following properties.

Exchange capacity: 1.16 meq/ml

Moisture content: 44.1% by mass

In this connection, an intermediate 7-bromoheptylstyrene was fractionated by distillation at 120° C. at a pressure of 0.4 Torr.

COMPARATIVE SAMPLE 2

An anion exchange resin (an example in which A in the formula (1) had 10 carbon atoms) was obtained in the same manner as in Production Example 1, except that 1,9-dibromononane was used instead of 1,3-dibromopropane in the synthesis of a ω-halogenoalkylstyrene. The resulting resin had the following properties.

Exchange capacity: 0.91 meq/ml

Moisture content: 40.3% by mass

In this connection, an intermediate 10-bromodecylstyrene was fractionated by distillation at 130° C. at a pressure of 0.2 Torr.

EXAMPLE 1

A total of 390 ml (swollen with water) of the anion exchange resin obtained in Production Example 1 was charged into a stainless steel tubular reactor 10 mm in inner diameter and 5000 mm in length. Metal meshes were then arranged at both ends of the tubular reactor to prevent the resin from flowing out of the system, and a back pressure valve was placed on an upper end (outlet side) of the reactor to maintain the pressure inside the reactor at about 1 MPa. The tubular reactor was then immersed in an oil bath at 70° C.

Next, a mixture containing 235 g of acrylic acid, 145 g of ethylene oxide, and 2 g of hydroquinone monomethyl ether was continuously introduced into the tubular reactor from the lower end thereof. The above amounts were those of components fed to the reactor per hour. The mixture was passed through the tubular reactor until the composition of a fluid flown out of the rector became constant. The resulting reaction products flown out of the outlet of the reactor were analyzed to find that 69% by mass of acrylic acid was converted into 2-hydroxyethyl acrylate. The fluid flown out of the reactor was colorless.

EXAMPLE 2

The procedure of Example 1 was repeated, except that the resin obtained in Production Example 2 instead of the resin obtained in Production Example 1 was charged into the stainless steel tubular reactor. An analysis of reaction products flown out of the outlet of the tubular reactor (stainless steel tube) revealed that 63% by mass of acrylic acid was converted into 2-hydroxyethyl acrylate. A liquid flown out of the tubular reactor was colorless.

COMPARATIVE EXAMPLE 1

The procedure of Example 1 was repeated, except that the resin to be charged into the tubular reactor was changed to the resin of Comparative Sample 1. An analysis of reaction products flown out of the outlet of the tubular reactor (stainless steel tube) revealed that the conversion rate from acrylic acid into 2-hydroxyethyl acrylate was 58% by mass, and was lower than that of Example 1. In addition, a liquid flown out of the tubular reactor was somewhat colored (yellowish).

COMPARATIVE EXAMPLE 2

The procedure of Example 1 was repeated, except that the resin to be charged into the tubular reactor was changed to the resin of Comparative Sample 2. An analysis of reaction products flown out of the outlet of the reactor (stainless steel tube) revealed that the conversion rate from acrylic acid into 2-hydroxyethyl acrylate was 49% by mass, and was lower than that of Example 1. A liquid flown out of the reactor was, however, colorless.

The present invention is configured as above, in which an anion exchange resin composed of a crosslinked polymer insoluble in a reaction system (reaction materials and products) is used as a catalyst to make the separation of reaction products from the catalyst easy. The invented process can therefore efficiently produce hydroxyalkyl (meth)acrylates, and concurrently, can effectively inhibit, for example, deterioration in properties of distillation residue due to transportation (contamination) of the catalyst into a distillation process.

Especially, the anion exchange resin for use as a catalyst in the invention is thermally and chemically stable and does not invite products to be colored due to elimination of functional groups. Such coloring problems occur when conventional anion exchange resins are used.

In addition, the aforementioned anion exchange resin is stable for a long time even under high temperature conditions, and is insoluble in a reaction system (reaction materials and products), and can be therefore easily separated from the reaction products. When the reaction is performed in a batch system, the anion exchange resin can be recycled and used as a catalyst for a long time. If the reaction is carried out in a continuous system, the resin can be continuously used for a long time. Thus, the invented process can economically and efficiently yield hydroxyalkyl (meth)acrylates.

Other embodiments and variations will be obvious to those skilled in the art, and this invention is not to be limited to the specific matters stated above.

What is claimed is:

1. A process for producing hydroxyalkyl (meth) acrylates by the reaction of (meth) acrylic acid with an alkylene oxide, in which an anion exchange resin is used as a catalyst said anion exchange resin containing a repeating unit represented by the following formula (1) as a component:

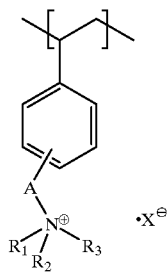

(1)

wherein A is a straight chain alkylene group having 3 to 8 carbon atoms, each of $R^1$, $R^2$, and $R^3$ is a hydrocarbon group or an alkanol group having 1 to 4 carbon atoms, which may be substituted with a hydroxyl group, $X^-$ is a counter ion coordinated with an ammonium group, where said substituent A with the ammonium group may be substituted at any position of a benzene ring, and said benzene ring may be substituted with an alkyl group or a halogen atom.

2. The process according to claim 1, wherein said straight chain alkylene group A in the formula (1) is a butylene group.

3. The process according to claim 1, wherein said anion exchange resin is a polymer being insoluble in a reaction system of (meth)acrylic acid and the alkylene oxide.

4. The process according to claim 1, wherein $X^-$ in the formula (1) is a salt form of the material-(meth)acrylic acid, of the product-hydroxyalkyl (meth)acrylate, or of both.

5. The process according to claim 1, wherein said anion exchange resin is obtained by the polymerization of monomers containing a crosslinkable monomer, said crosslinkable monomer having two or more ethylenically unsaturated double bonds being radical-polymerizable.

6. The process according to claim 5, wherein said anion exchange resin is obtained by the polymerization of monomers containing 0.1% to 50% by mass of the crosslinkable monomer relative to the total mass of said monomers.

7. The process according to claim 1, wherein said alkylene oxide is ethylene oxide or propylene oxide.

8. The process according to claim 1, wherein the alkylene oxide is used in an amount of one to five times by mass that of the (meth)acrylic acid.

\* \* \* \* \*